(12) United States Patent
Rojas et al.

(10) Patent No.: US 6,773,727 B1
(45) Date of Patent: Aug. 10, 2004

(54) USE OF GOSSYPOL AND RELATED TERPENES FOR CONTROL OF URBAN AND AGRICULTURAL PESTS

(75) Inventors: Maria G. Rojas, Metairie, LA (US); Juan A. Morales-Ramos, Metairie, LA (US); Peter J. Wan, Metairie, LA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 62 days.

(21) Appl. No.: 09/928,585

(22) Filed: Aug. 13, 2001

(51) Int. Cl.$^7$ .................. A01N 35/04; A01N 35/06; A01N 43/08; A01N 43/16; A01N 65/00

(52) U.S. Cl. .................. 424/725; 424/93.5; 424/773; 424/774; 424/776; 424/778; 424/779; 424/DIG. 11; 514/27; 514/451; 514/452; 514/453; 514/456; 514/457; 514/458; 514/464; 514/465; 514/468; 514/474; 514/475; 514/680; 514/681; 514/700; 514/715; 514/724; 514/729; 514/739; 514/762; 514/763; 514/766; 43/121; 43/132.1

(58) Field of Search .................. 424/84, 93.5, 725, 424/773, 774, 776, 778, DIG. 11; 514/27, 451–453, 456–458, 464, 465, 468, 474, 475, 680, 681, 700, 715, 724, 729, 739, 762, 763, 766; 43/121, 132.1

(56) References Cited

U.S. PATENT DOCUMENTS 3,954,968 A * 5/1976 McKibben .................. 424/84
6,316,017 B1 * 11/2001 McKibben et al. ......... 424/410

FOREIGN PATENT DOCUMENTS

| EP | 49705 | * | 4/1982 |
| WO | 99/08529 | * | 2/1999 |

OTHER PUBLICATIONS

Chemical Abstracts 102:201189 (1985).*

WPIDS Abstract, accession No. 1992–406126, abstracting SU 1703030 (1992).*

* cited by examiner

*Primary Examiner*—John Pak
(74) *Attorney, Agent, or Firm*—John D. Fado; Randall E. Deck

(57) ABSTRACT

Low concentrations of gossypol and related phyllophage toxins from cotton improve the effectiveness of insecticidal agents against social insects, including cockroaches, and particularly termites and ants. Levels of gossypol and other cotton phyllophage toxins which are sufficiently low as to be non-biocidal to social insects alone, will significantly increase the control efficacy of other insecticidal agents. Consequently, use of these low levels of these cotton phyllophage toxins allows the levels of insecticidal agents necessary for effectively controlling the insects to be significantly reduced relative to applications without cotton phyllophage toxins. Furthermore, insecticidal agents which are normally ineffective for control of social insects when used alone, may be effective when used in conjunction with the cotton phyllophage toxins.

29 Claims, No Drawings

USE OF GOSSYPOL AND RELATED TERPENES FOR CONTROL OF URBAN AND AGRICULTURAL PESTS

BACKGROUND OF THE INVENTION

1. Field of the Invention

The invention relates to compositions and methods effective for control of social insects such as termites, fire ants, and cockroaches.

2. Description of the Prior Art

Cotton plants, especially the seed, are a rich source of gossypol and related terpenes. Cotton is a major cash crop of the Southern states of the U.S. Cotton seed (a by-product) with an annual production of 7 million tons in the U.S. and 36 million tons worldwide, has long been processed into edible oil and protein feed meals. Due to the presence of gossypol, a known antinutritional factor to nonruminant animals, the protein meals are primarily used as feed to ruminants. Processing technologies (Gardner, H. K., et al., "Advanced liquid cyclone process for edible cotton seed flour production," [1973]*E. Oil Mill Gaz.* 78:12–17; Freeman et al., "Advanced air classification of defatted, glanded cotton seed flours to produce edible protein product," [1979] *J. Food Sci.* 44:1522–1524) have been developed at the U.S. Department of Agriculture to reduce the concentration of gossypol in the finished meal. A cotton seed meal produced by these processes can be used as a food ingredient as long as it contains no more than 450 ppm free gossypol, a limit established by the research effort of the Southern Regional Research Center, ARS-USDA, New Orleans, La. (Code of Federal Regulations 21.172.894).

Glandless cultivars, through conventional breeding, are subject to attack by beet armyworm (*Spodoptera exigua* [Hubner]), bollworm (*Heliothis zea* [Boddie]), grape colaspis (*Maecolaspis flavida* [Say]), cutworms (undetermined species), and pill bugs (Porcellio spp.). Rodents also attacked glandless bolls and ate glandless cotton seed more aggressively than the glanded seed as (Bottger et al., "Relation of gossypol content of cotton plants to insect resistance," [1964] *J. Econ. Entomol.* 57:283–285). Gossypol is also toxic to cotton aphids (*Aphis gossypii* Glover), lygus bugs (*Lygus hesperas* Knight), salt-marsh caterpillars (*Estigmene acrea* [Drury]), thurberia weevils (*Anthonomus grandis thurberiae* Pierce), and bollworms (Bottger et al., 1964, supra). Jenkins et al. ("The comparative preference of insects for glanded and glandless cottons," [1966] *J. Econ. Entomol.* 59:352–356), showed that grape colaspis and leaf beetle (*Gastrophysa cyanea* Melsheimeriae) preferred feeding on glandless compared to glanded cotton cultivars, and cotton leafworm moths (*Alabama argillacea* [Hubner]) preferred to oviposit on glandless lines.

In addition to gossypol, several other toxic terpenoids (generally referred to as terpenoid aldehydes) are found in the glands in foliar tissue of cotton plants, including p-hemigossypolone, p-hemigossypolone-6-methyl ether, heliocide $H_1$, heliocide $H_2$, heliocide $H_3$, heliocide $H_4$, heliocide $B_1$, heliocide $B_2$, heliocide $_3$, and heliocide $B_4$.

The effective dosage ($\mu$moles/g diet) of toxic terpenoids required to reduce by 50% the growth of the tobacco budworm (*Heliothis virescens* [F.]) larvae fed an artificial diet have been determined for several of these compounds as follows: heliocide $H_1$, 2.5; heliocide $H_2$, 11.2; heliocide $H_3$, 3.9; heliocide $B_1$, 4.6; hemigossypolone, 10.5; and gossypol, 0.8 (Stipanovic et al., "Natural insecticides from cotton (Gossypium)", [1977]*ACS Symposium Series, No. 62, Host Plant Resistance to Pests*, 197–214). Hemigossypolone-6-methyl ether and heliocides $B_2$ and $B_3$ had no effect on growth at 2.5 $\mu$moles/g diet. In this study, gossypol was the most toxic compound with heliocides $H_1$ and $H_3$ a close second and third. Conversion to the 6-methyl ether derivative consistently reduced toxicity. In contrast, field studies have shown that the levels of heliocides and hemigossypolone correlate better with resistance than the gossypol levels (Hedin, P. A. et al., "Relationship of glands, so cotton square terpenoid aldehydes and other allelochemicals to larval growth of *Heliothis virescens* [Lepidoptera: Noctuidae]," [1992] *J. Econ. Entomol.* 85:359–364; Jenkins, J. N., "Host resistance to insects in cotton," [1995] *in Proceedings of the World Cotton Research Conference*-1, edited by G. A. Constable and N. W. Forrester, Melbourne, Australia, pp. 359–372).

In addition to the terpenoid aldehydes, the volatile mono- and sesquiterpenes also occur exclusively in the foliar glands. Damaged glandless plants can also produce terpenes, but in much smaller amounts. The volatile terpene caryophyllene oxide interacts synergistically with gossypol to retard tobacco budworm larval growth (Gunasena et al., "Effects of caryophyllene, caryophyllene oxide, and their interaction with gossypol on the growth and development of *Heliothis virescens* [F.][Lepidoptera: Noctuidae]," [1988] *J. Econ. Entomol.* 81:93–97; Williams et al., "Effects of gossypol and other cotton terpenoids on *Heliothis virescens* development," [1987]*Rev. Latinoamer. Quim.* 18:119–131), but the related sesquiterpene caryophyllene does not act synergistically. When glands are eaten, insects consume the terpenoid aldehydes along with a diverse mixture of monoterpenoids.

Several other low molecular weight compounds and condensed tannins have been implicated as possible factors in insect resistance. Hedin et al. ("Cyanidin-3 $\beta$-Glucoside, a newly recognized basis for resistance in cotton to the tobacco budworm *Heliothis virescens* (Fab.)," [1983] *Experientia* 39:799–801), have identified cyanidin-3$\beta$-glucoside in the glands. This and various other allelochemicals (i.e., condensed tannins, flavonoids, and cyclopropene fatty acids) have been evaluated for their effect on bollworms and budworms (Shaver, T. N. and Lukefahr, M. J., "Effects of flavonoids pigments and gossypol on growth and development of the bollworm, tobacco budworm, and pink bollworm," [1969]*J. Econ. Entomol.* 62:643–646; Elliger et al., "Relative toxicity of minor cotton terpenoids compared to gossypol, " [1978] *J. Econ. Entomol.* 71:161–164; Chan et al., "Inhibition of lepidopterous larval growth by cotton constituents," [1978] *Entomol. Exp. Appl.* 24:94–100; Chan et al., "Condensed tannin, an antibiotic chemical from *Gossypium hirsutum*," [1978]*J. Insect Physiol.* 24:113–118; Chan et,al., "A rapid diet preparation method for antibiotic phytochemical bioassay," [1978] *J. Econ. Entomol.* 71:366–368; Hedin et al., "The chemical basis for resistance in cotton to *Heliothis insects*," [1981] In *Regulation of Insect Development and Behavior*, M. Kloza, Ed., Wroclaw Univ. Press, pp. 1071–1086; Hedin et al., "Effects of cotton plant allelochemicals and nutrients on behavior and development of tobacco budworm," [1991]*J. Chem. Ecol.* 17:11–7–1121; Jenkins et al., "Cotton allelochemicals and growth of tobacco budworm larvae," [1983] *Crop Sci.* 23:1195–1198). These compounds also can play a role in insect resistance. Reports in the literature comparing glandless and glanded plants may refer to the gossypol content of the latter, but actually refer to all of the terpenoid aldehydes in the gland. Cotyledonary leaves are an exception, since the terpenoid aldehyde present in this tissue is almost exclusively gossypol.

Bollworms and tobacco budworms grow better on glandless than on glanded cottons. However, differences in infestations of cotton fleahoppers (*Psallus seriatus* [Reuter]) and the boll weevil (*Anthonomus grandie* Boheman) between glanded and glandless plants were small or non-existent. Lukefahr and Martin (1966), supra, found that gossypol was equally toxic to bollworm and tobacco budworm larvae. Bottger, G. T. and Patana, R. ("Growth, development, and survival of certain lepidoptera fed gossypol in the diet," [1966] *J. Econ. Entomol.* 59:1166–1168), found the beet armyworm, bollworm, cabbage looper (Trichoplusiani [H übner]) and salt-marsh caterpillar grew slower on diets containing gossypol acetate. Gossypol appears to deter many lepidopterous pests of cotton.

Spiny bollworm (*Earias insulana* Boisduval), which is a major cotton pest in Israel, also causes more damage on glandless cottons in the field (Meisner et al., "The effect of gossypol on the larvae of the spiny bollworm, *Earias insulana*," [1977] *Ent. Exp. and Appl.* 22:301–303). In bolls containing 0.58% gossypol, 45% pupated, but at 2.34% gossypol, only 9% pupated. Dongre, T. K. and Rahalkar, G. W. ("Growth and development of spotted bollworm, *Earias vittella* on glanded and glandless cotton and on diet containing gossypol," [1980] *Entomol. Exp. & Appl.* 27:6–10) found similar results with the spotted bollworm. Feeding on glandless cotton leaves treated with a 1% gossypol solution gave similar results. With the cotton leafworm (*Spodoptera littoralis* [Boisduval]), the effect was even more dramatic (Meisner, J. et al., "Phagodeterrency induced by pure gossypol and leaf extracts of a cotton strain with high gossypol content in the larva of *Spodoptera littoralis*," [1977] *J. Econ. Entomol.* 70:149–150; Meisner, J. et al., "The response of *Spodoptera littoralis* larvae to gossypol incorporated in an artificial diet," [1977] *Environ. Entomol.* 6:243–244; Meisner, J. et al., "The response of *Spodoptera littoralis* larvae to gossypol incorporated in an artificial diet," [1977] *Environ. Entomol.* 6:243–244). With 0.5% gossypol in the diet, mortality was nearly 70% after 10 days and only 0.3% of the larvae eventually pupated; 1.0% gossypol strongly suppressed feeding (Meisner, J. et al., "The response of *Spodoptera littoralis* larvae to gossypol incorporated in an artificial diet," [1977] *Environ. Entomol.* 6:243–244). Larval growth and development of the native budworm (*Heliothis punctigera* Wallengren) and the cotton bollworm *Heliothis armigera* (Hübner) are also inhibited by gossypol (Kay, I. R. et al., "The effect of gossypol in artificial diet on the growth and development of *Heliothis punctigera* Wallengren and *H. armigera* (Hübner) (Lepidoptera: Noctuidae)," [1979] *J. Aust. Ent. Soc.* 18:229–232).

Gossypol has an antifeedant effect. Shaver and Parrott found development was less affected by gossypol when larvae were allowed to first feed on standard diet (Shaver, T. N. and Parrott, W. L., "Relationship of larval age to toxicity of gossypol to bollworms, tobacco budworms, and pink bollworms" [1970] *J. Econ. Entomol.* 63:1802–1804). Older larvae were either less deterred from eating or were better able to detoxify the gossypol. Shaver et al. ("Food utilization, ingestion, and growth of larvae of the bollworm and tobacco budworm on diets containing gossypol," [1970] *J. Econ Entomol.* 63:1544–1546) showed that bollworms (5-day-old) utilized a high glanded diet less efficiently than low glanded or glandless diets, and growth was retarded. A diet containing an acetone extract from the high glanded cultivar was also utilized less efficiently and there was a decrease in larval weight. With bollworms, at 0.15% gossypol, in an artificial diet, food utilization by the bollworm was decreased from 54.5% on the regular diet to 42.5% on the gossypol diet. With tobacco budworms, gossypol at the 0.15% level did not measurably affect food utilization. However, when the level was increased to 0.30%, food consumption of both 5- and 8-day-old larvae was impaired.

Oliver et al. conducted studies to determine how glanded and glandless cotton flower buds (squares) were utilized by the bollworm (Oliver, B. F. et al., "Utilization of glanded and glandless cotton diets by the bollworm," [1970] *J. Econ. Entomol.* 63:1965–1966). They studied four stages of larvae that were first raised on a control diet. Larvae that weighed approximately 60, 110, 150, or 192 mg were placed on diets containing freeze-dried squares. Larvae were allowed to feed for 48 hours. All four sizes of larvae gained less weight when transferred to the glanded diet, and they consumed 20–31% less diet. Growth of the smallest was most inhibited due to a reduced efficiency of food conversion to body mass. The efficiency of food conversion for larvae of different weights compared to larvae on glandless diets was as follows: 60 mg, 51%; 120 mg, 64%; 150 mg, 82%; and 198 mg, 97% as efficient. Thus, both a reduction in food consumption and in efficiency of food conversion were responsible for the reduced weight gain. The higher efficiency of food conversion of older larvae explains the 1970 report by Shaver and Parrott on the modest effect of gossypol on older larvae. Further studies in 1987 by Parrott et al. showed that tobacco budworm neonate larvae fed gossypol at 0.02% in an artificial diet for nine days were only slightly smaller (98%) than the control (Parrott, W. L. et al., "Feeding and recovery of gossypol and tannin from tobacco budworm larvae," [1987] *Southwest. Entomol.* 12:197–204). However, at 0.06% and 0.2% gossypol in the diets, the weights were only 63% and 13% of the controls, respectively. Essentially no gossypol could be recovered from any of the larvae themselves at any dietary level.

Mulrooney et al. found the efficiency of conversion of digested food to body weight was lower for tobacco budworm in cultivars with higher levels of gossypol, implying that energy is being diverted for detoxification processes (Mulrooney, J. E. et al., "Nutritional indices of second-instar tobacco budworm larvae [Lepidoptera: Noctuidae] fed different cotton strains," [1985] *J. Econ. Entomol.* 78:757–761).

Glands have a similar effect on the cotton leafworm (*A. argillacea*) (Johnson, S. J., "Larval development, consumption, and feeding behavior of the cotton leafworm, *Alabama argillacea* (Hübner)," [1984] *Southwest. Entomol.* 9:1–6).

In a related study, Rojas et al. (1992) studied the metabolic fate of radiolabelled $^{14}C$ gossypol in the tobacco budworm diet (Rojas, M. G. et al., "Metabolism of gossypol by *Heliothis virescens* [F.] [Lepidoptera: Noctuidae]," [1992] *Envir. Entomol.* 21:518–526; Rojas, M. G. et al., "A method for the preparation of labelled gossypol by the incorporation of $^{14}C$ Acetate," [1989] *J. Labelled Comp. Radiopharm.* 27:995–998). The radioactivity was mainly found in the fat body of fifth-stadium larvae, the dissolved tissues of pupae, the abdomen of newly-emerged moths, and the larval frass. Labeled gossypol was eliminated as a respiration product from third to fifth instars, and from prepupa to adult. Gossypol was excreted in the larval frass as a free compound and as a conjugate. High-performance liquid chromatography (HPLC) analyses of the radiolabelled frass indicated that the ethyl acetate and methyl alcohol extracts contained the highest concentrations of free and conjugated gossypol, respectively. Two metabolites from the tobacco budworm larval frass were isolated and identified as derivatives of gossypol containing six glucose moieties attached to the gossypol nucleus, and a derivative of methyl parasept (diet preservative) containing one glucose moiety (Rojas, M. G. et al., "A detoxification product of the xenobiotic methyl parasept by *Heliothis virescens* [F.] [Lepidoptera: Noctuidae]," [1990] *Comp. Biochem. Physiol.* 96C:281–285). This suggests that for the specialist feeder, excretion is the preferred method of elimination, rather than detoxification. Gossypol may be toxic to both insects, but the cotton leafworm more efficiently excretes gossypol. Thus, the harmful effects are minimized and the energy required to detoxify it is less.

Meisner et al. (1978) found that gossypol inhibits protease and amylase activity, but does not affect invertase activity in the cotton leafworm (*S. littoralis*) (Meisner, J. et al., "Gossypol inhibits protease and amylase activity of *Spodoptera littoralis* larvae," [1978] *Ann. Entomol. Soc. Amer.* 71:5–8). Gossypol appeared to interact with both the enzyme substrate (i.e., casein) and with the protease enzyme. They concluded that either or both mechanisms could account for gossypol's activity.

Studies by Hedin et al. (1988) strongly support the concept that gossypol acts as both a toxicant and an antifeedant, especially in the early instars (Hedin, P. A. et al., "Elucidating mechanisms of tobacco budworm resistance to allelochemicals by dietary tests with insecticide synergists," [1988] *Pest. Biochem. Physiol.* 32:55–61). They studied the interaction of gossypol with piperonyl butoxide, an insecticide synergist that enhances insecticidal action by inhibiting the insect's mixed function oxidases (MFOS). Gossypol alone reduced the growth of all these groups of larvae. When piperonyl butoxide was added to the gossypol, the larvae were significantly smaller than with the gossypol alone. Since piperonyl butoxide at 0.02% in the diet had little effect on larval growth, the authors concluded that MFOs are probably involved. They also concluded that gossypol probably acts as an antifeedant, especially in the early instars. Williams et al. (1987), supra, report the same reduction in feeding by tobacco budworm first instar larvae and a synergistic. effect when gossypol is combined with caryophyllene oxide.

Several studies support the concept that gossypol acts as an antifeedant to early instars (Waiss, A. C. et al., "Biological active cotton constituents and their significance in host plant resistance," [1981] *Proc. Beltwide Cotton Prod. Res. Conf.*, New Orleans, La., p. 61; Parrott, W. L. et al., "Feeding behavior of first-stage tobacco budworm [Lepidoptera: Noctuidae] on three cotton cultivars," [1983] *Ann. Entomol. Soc. Amer.* 76:167–170); Hedin et al. [1992], supra).

Raulston et al. (1985) observed a significant increase in budworm tolerance to gossypol during thirteen generations (Raulston, J. R. et al., "Tobacco budworms: response to gossypol and selection in a field-collected strain under laboratory conditions," [1985] *J. Econ. Entomol.* 78:158–162).

Vilkova et al. (1989) reported that even though high gossypol lines had a detrimental effect on cotton bollworm development, survival and larval weight when compared to those on low gossypol lines, the larvae from the high gossypol lines that survived had a higher pupal weight because of their apparent resistance to gossypol, but fecundity of these survivors was significantly reduced (Vilkova, N. A. et al., "Effect of cotton cultivars with high content of goeBypol on development of the cotton bollworm, *Heliothis armiqera* [Hbn.][Lepidoptera: Noctuidae]," [1989] *Entomol. Rev.* 68:129–137).

Several studies suggest that gossypol induced resistance to insecticides. Abou-Donia et al. (1974) found that topical treatment of a solution of gossypol in acetone to fourth instar larvae of the cotton leafworm (*S. littoralis*) increased the $LD_{50}$ dosage from two to three times the $LD_{50}$ for untreated larvae for four different insecticides (Abou-Donia, M. B. et al., "Gossypol: antagonistic effect on toxicity of insecticides to *Spodoptera littoralis*," [1974] *Experientia* 15:1151–1152). In an artificial diet study, gossypol concentrations were negatively correlated with the toxicity of methyl parathion to budworm larvae (Shaver, T. N. and Wolfenbarger, D. A., "Gossyol: influence on toxicity of three insecticides to tobacco budworm," [1976] *Environ. Entomol.* 5:192–194). When leaves of a high gossypol plant were treated with phosfolan, mortality of cotton leafworm larvae was lower compared to a glandless cultivar (Meisner et al., "The response of *Spodoptera littoralis* larvae to gossypol incorporated in an artificial diet," [1977] *Environ. Entomol.* 6:243–244).

Biosynthesis of terpenoids related to gossypol are induced in cotton when it is attached by various fungal pathogens (Daayf, F. M. et al., "Early vascular defense reactions of cotton roots infected with a defoliating mutant strain of *Verticillium. dahliae*," [1997] *Euro. J. Plant Path.* 103:125–136; Cui, Y. et al., "Expression of potential defense response genes in cotton," [2000] *Physiol. Mol. Plant Path.* 56:25–31). Insect damage appears to induce chemical changes in the foliage and induction of volatile terpenes (Loughrin, J. H. et al., "Diurnal cycle of emission of induced volatile terpenoids by herbivore-injured cotton plants," [1994] *Proc. Nat'l Acad. Sci.* 91:11836–11840; McCall, P. J. et al., "Herbivore-induced volatile emissions from cotton [*Gossypium hirsutum* L.] seedlings," [1994] *J. Chem. Ecol.* 20:3039–3059; Donath, J. and Boland, W., "Biosynthesis of acyclic homoterpenes: enzyme selectivity and absolute configuration of the nerolidol precursor," [1995] *Phytochemistry* 39:785–790; Rose, U. S. R. et al., "Volatile semiochemicals released from undamaged cotton leaves," [1996] *Plant Physiol.* 111:487–495; Pare, P. W. and Tumlinson, J. H., "Cotton volatiles synthesized and released distal to the site of insect damage," [1998] 47:521–526).

Alborn et al. (1996) reported that the beet armyworm larvae prefer young undamaged leaves to undamaged young leaves from a previously damaged plant (Alborn, H. T. et al., "Systemic induction of feeding deterrents in cotton plants by feeding of *Spodoptera* Spp. larvae," [1996] *J. Chem. Ecol.* 22:919–932). See also, McAuslane, H. J. et al., "Systemic induction of terpenoid a aldehydes in cotton pigment glands by feeding of larval *Spodoptera exigua*," (1997) *J. Chem. Ecol.* 23:2861–2879. HPLC analysis revealed higher concentrations of hemigossypolone and heliocides $H_1$ and $H_2$ per gland in foliage of these damaged plants. When compared to leaves from undamaged plants, heliocide $H_2$ showed the largest change with over a three-fold increase in concentration.

In 1998, McAuslane and Alborn found a 33-fold increase in preference for undamaged terminal leaves from undamaged glanded plants by beet army worm larvae (McAuslane, H. J. and Alborn, H. T., "Systemic induction of allelochemicals in glanded and glandless isogenic cotton by Spodoptera exigua feeding," [1998] *J. Chem. Ecol.* 24:399–416). Extracts from the terminal foliage contained significantly higher concentrations of hemigossypolone, gossypol and the heliocides. Of these compounds, heliocides $H_1$ and $H_4$, which are derived from the reaction of hemigossypolone and β-ocimene, had the largest percentage increase, 351% and 487% respectively. Hemigossypolone had an increase of 149%, gossypol increased by 124% and heliocides $H_2$ and $H_3$ increased by 42% and 45%, respectively. They also noted an increase in volatile compounds from the damaged plants. Among the monoterpenes, β-ocimene and myrcene had the largest increases of greater than six-fold and four-fold, respectively; these compounds react with hemigossypolone to give heliocides $H_1$ and $H_4$, and heliocides $H_2$ and $H_3$, respectively. α-Pinene, β-pinene and limonene increased by 3.2–3.6-fold. Damaged glanded plants released more than twice as many terpenes as undamaged plants.

Gossypol is largely excreted in the bound form, and thus decreases the nutritional value of the plant material. Studies with non-ruminant animals have shown that gossypol binds to free amino groups in proteins such as in lysine and thereby reduces the nutritional value of the feed. The same appears to be true for the budworm (Meisner et al. [1978]; supra). Terpenoid aldehydes did not increase in wounded tissue itself.

Gossypol does not appear to provide the plant with any protection from boll weevil (Lukefahr, M. J. et al., "Growth and infestation of bollworms and other insects on glanded and glandless strains of cotton," [1966] *J. Econ. Entomol.* 59:817–820). Parrott et al. (1969) concluded boll weevils seemed to be attracted to and feed on plants that contain gossypol (Parrott, W. L. et al., "Preference studies with hosts and nonhosts of the boll weevil, *Anthonomus grandis*," [1969] *Ann. Entomol. Soc. Amer.* 62:261–264). Gossypol and caryophyllene both suppress bacteria in the boll weevil's gut and egg hatch of boll weevils reared on a diet containing gossypol was improved over those reared on a diet without gossypol (Hedin, P. A. et al., "Suppressants of gut bacteria in the boll weevil from the cotton plant," [1978] *Econ. Entomol.* 71:394–396).

Davidson et al. (1996) found gossypol did not affect mortality or honeydew production of silverleaf whitefly (*Bemisia argentifolii* Bellows and Perring) (Davidson, E. W. et al., "Activity of natural toxins against the silverleaf whitefly *Bemisia argentifolil*, using a novel feeding bioassay system," [1996] *Entomol. Exper. Appl.* 79:25–32). Almeida (1980) suggested that there appears to be an optimum value of gossypol for normal development of cotton strainer bug (*Dysdercus fasciatus* Signoret) (Almeida, A. A., "Influence of the glandless and glanded cotton seeds on development", fecundity and fertility of *Dysdercus fusciatus signoret* [Hemiptera Pyerhocoridae] [1980] *Rev. Brasil. Biol.* 40:659–662).

Karban and Carey (1984) found that spider mite (*Tetranychus urticae* Koch) populations were reduced on new growth of cotton seedlings whose cotyledonary leaves had previously been exposed to mites, as compared to plants that had never been exposed to mites.

Gossypol acts as a male antifertility agent in humans en and adversely affects a host of enzymes. These various toxicological/biological effects in animals are due primarily or perhaps exclusively to the (−)-enantiomer of gossypol.

Baiting compositions not containing gossypol for controlling termites are known, as described in U.S. patent application Ser. Nos. 09/625,940 filed Jul. 26, 2000, Ser. No. 09/294,499 filed Apr. 20, 1999, and Ser. No. 09/748,036 filed Dec. 22, 2000, the contents of each of which are incorporated herein by reference.

SUMMARY OF THE INVENTION

We have discovered that low concentrations of gossypol and related phyllophage toxins from cotton improve the effectiveness of insecticidal agents against social insects, including cockroaches, and particularly termites and ants. Levels of gossypol and other cotton phyllophage toxins which are sufficiently low as to be non-biocidal to social insects alone, will significantly increase the control efficacy or activity of other insecticidal agents. Consequently, use of these low levels of these cotton phyllophage toxins allows the levels of insecticidal agents necessary for effectively controlling the insects to be significantly reduced relative to applications without cotton phyllophage toxins. Furthermore, insecticidal agents which are normally ineffective for control of social insects when used alone, may be effective when used in conjunction with the cotton phyllophage toxins. Low, non-biocidal concentrations of gossypol or the other cotton phyllophage toxins may be formulated into a bait, alone or in combination with the other insecticidal agents. Alternatively, the other insecticidal agents may be formulated into separate baits which are applied in the vicinity of the gossypol or cotton phyllophage toxin containing bait, such that both baits are subject to consumption by the target insects.

In accordance with this discovery, it is an object of this invention to provide compositions and methods for controlling social insects.

Another object of this invention is to provide compositions and methods for controlling termites, ants, or cockroaches.

It is also an object of the invention to provide compositions and methods for controlling social insects such as termites, ants, and cockroaches using reduced levels of insecticides.

Other objects and advantages of this invention will become readily apparent from the ensuing description.

DETAILED DESCRIPTION OF THE INVENTION

According to this invention, there is provided compositions which include gossypol and/or other phyllophage toxins from glanded cotton (collectively referred to herein as cotton phyllophage toxins), in low concentrations which, in the absence of other insecticidal agents, are not biocidal to the target insects (i.e., at concentrations which are non-lethal and will not kill the target insects). As described herein, a phyllophage toxin is a plant-produced compound which kills or debilitates organisms which feed on leaves. We have unexpectedly discovered that at these low levels, gossypol and other cotton phyllophage toxins slowly weaken the target insects when ingested, thereby rendering them susceptible to a variety of other insecticidal agents at significantly lower levels than normally required for toxicity, and may even render the target insects susceptible to insecticidal agents which are normally ineffective. Moreover, at these low levels, the gossypol and other cotton phyllophage toxins may synergistically enhance the insecticidal efficacy of these other insecticidal agents. Further still, ingestion of these low levels of cotton phyllophage toxins may also increase the susceptibility of the target insects to attack by naturally occurring fungi, bacteria, and predators, such as ants, spiders, and centipedes. In contrast to some conventional insecticidal compositions which are repellent to the target insects, the cotton phyllophage toxins used at the low levels described herein are readily accepted and consumed by the target insects; the compounds do not exhibit any repellency toward the target insects.

The compositions of the present invention are effective in controlling a variety of economically important social insects, including termites, roaches, and ants. The compositions are particularly effective for control of fire ants, including Solenopsis invicta, *S. germinata*, and *S. xyloni*, black ants, including *Tapinoma sessile*, and other ants, cockroaches, including *Periplaneta americana, Blattella qermanica*, and *P. fuliginosa*, and most particularly subterranean termite species belonging to the families Rhynotermitidae and Kalotermitidae, most notably *Coptotermes formosanus, Reticulitermes flavipes*, and *R. virginicus*.

The phyllophage toxins of this invention derived from glanded cotton include gossypol, sugar derivatives of gossypol, and other terpenoids having fused ring, e.g., hemigossypol, desoxyhemigossypol, desoxyhemigossypol-6-methyl ether, hemigossypol-6-methyl ether, hemigossypolone, hemigossypolone-6-methyl ether, heliocide $H_1$, heliocide $B_1$, heliocide $H_4$, heliocide $B_4$, heliocide $H_2$, heliocide $B_2$, heliocide $H_3$, heliocide $B_3$, quercetin and rutin, pharmaceutical salts thereof, racemic mixtures and optical isomers thereof, and mixtures of any of the foregoing.

The structure of gossypol is shown below:

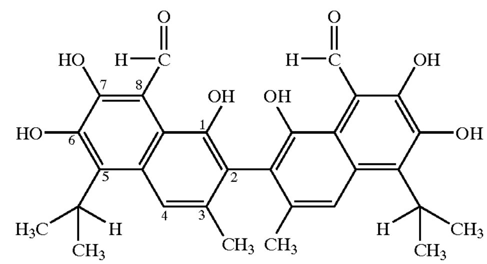

Gossypol

The structures of related compounds useful in this invention as phyllophage toxins are set forth in Scheme I which shows biosynthesis from desoxyhemigossypol to hemigossypol, or methylation of desoxyhemigossypol and its eventual conversion to heliocides $B_1$ to $B_4$.

Scheme I

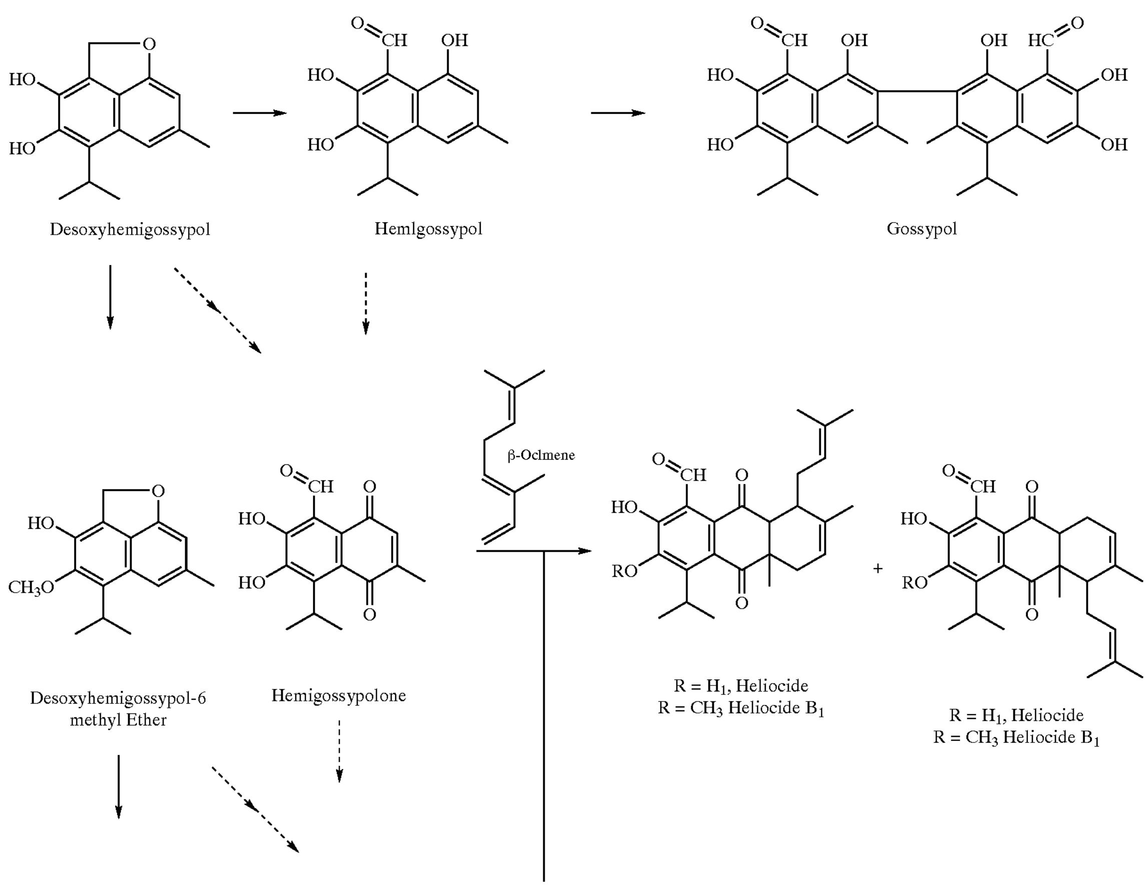

Desoxyhemigossypol

Hemlgossypol

Gossypol

β-Oclmene

Desoxyhemigossypol-6 methyl Ether

Hemigossypolone

R = $H_1$, Heliocide
R = $CH_3$ Heliocide $B_1$

R = $H_1$, Heliocide
R = $CH_3$ Heliocide $B_1$

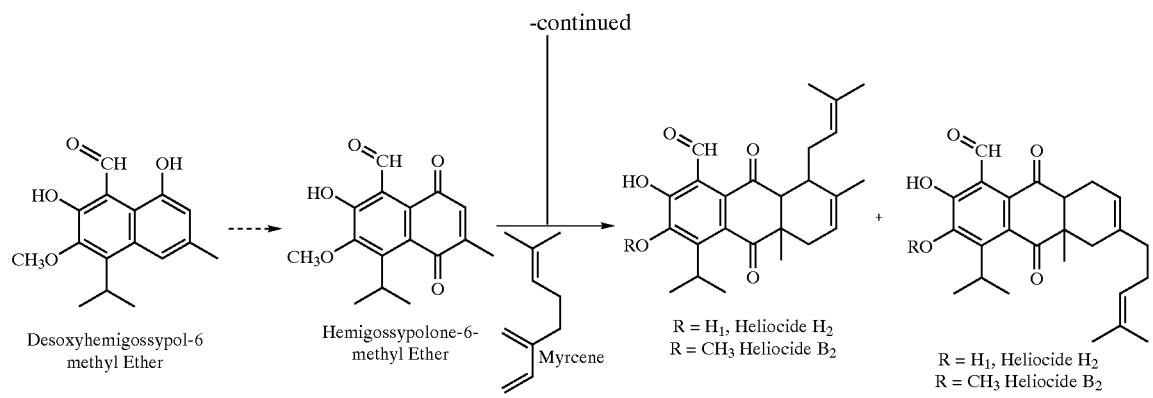

Gossypol and 1,1', 6,6', 7,7'-hexahydroxy-5,5'-diisopropyl-3, 3'-demethyl-(2,2'-binaphthalene)-8,8'-dicarboxyaldehyde are preferred compounds of this invention. L-gossypol, the (−) enantiomer, is most preferred. Gossypol actually makes the compositions more attractive to termites.

Formulations of the gossypol and related cotton phyllophage toxins may be prepared from these compounds in isolated, substantially pure form, or in impure form. However, as a practical matter, it is envisioned that commercial formulations will be prepared from directly crude forms of the compounds, such as various glanded cotton and cotton seed products. "Glanded cotton," as is known to the art, is cotton having glands capable of producing gossypol and related compounds. The pigment glands in cotton seed kernels are ovoid or spherical in shape with a size range between 100 to 400 microns on the long axis. They are generally bigger than protein particles and, therefore, can be separated faster than protein fraction in the air classification or liquid cyclone process.

A variety of cotton and cotton seed products are suitable for use herein as sources of the phyllophage toxins. For example, without being limited thereto, the phyllophage toxins may be incorporated into the pesticidal compositions by adding cotton seed, cotton seed meats, dark crude cotton seed oil, or oil derived from screw presses, cotton seed meal, cotton seed flour, miscella (mixed oil and solvent) resulting from cotton seed extraction processes, soap stock resulting from treating miscella or crude cotton seed oil with caustic, acid oil from sulfuric acid-treated soap stock, and meal resulting from treating residual solids from solvent extraction processes with soap stock.

Processes for obtaining the phyllophage toxin containing materials from cotton, and particularly cotton seeds, are well known in the art, and include pressing or solvent extraction, refining process or combinations thereof. Preferred solvents for extraction of gossypol are acetone, hexane, methanol, ethyl alcohol or ethyl acetate, most preferably acetone. Without being limited thereto, in a preferred process, the gossypol and other phyllophage toxins are obtained by a combined pressing and extraction process. By way of illustration, in accordance with one such process, white cotton seed is introduced into an extruder or expeller to partially separate the oil from the pressed cake. Normally, white cotton seed is cleaned to remove foreign matter and delinted to remove the short fuzzy linters and form "black seed" which is dehulled. Kernels (meats) are separated from the hulls, ground or flaked with a set of flaking rolls and subjected to heat (e.g., around 230° F.), and oil is expressed using an expeller or screw press to form crude oil and pressed cake. This is called a screw press operation with crude cotton seed oil and screw pressed meal being its final product. Pressed cake is ground and treated with a solvent mill to produce a miscella (mixed oil and solvent, e.g., about 24% oil and about 76% solvent) containing gossypol and other terpenoids. Both oil and expressed cake obtained this way can be used in compositions of this invention without further treatment. The oil has a gossypol content around 0.2–0.4% gossypol but still supplies sufficient gossypol and other terpenoids for use in this invention.

Solvent is removed from the miscella in an evaporator. Crude oil extruded from the cooked and flaked kernels is combined with the oil obtained from the miscella after it has been subjected to evaporation. The final product of this process is crude cotton seed oil, or once-refined oil, and defatted cotton seed meal.

Direct solvent extraction or expander solvent extraction processes may also be used to obtain gossypol and related terpenoid-rich products. In the Expander Solvent Extraction process, kernels are flaked and cooked at about 180° F. and fed to a low shear extruder, i.e., expander, to produce porous collets or pellets.

The porous collets are treated with a solvent such as hexane, isohexane, ethanol, isopropanol or acetone, with hexane being the most commonly used to form a defatted solid called MARC and miscella. Solvent is removed from the full miscella in an evaporator to about 50% oil content, followed by a caustic miscella refining step to form the once-refined cotton seed oil. The once-refined oil is also termed Prime Bleachable Summer Yellow (PBSY) oil by the trade. Some operators choose to completely remove the solvent and form the crude oil, which may be caustically refined to produce PBSY or traded in the market as crude oil. The MARC is desolventized and ground to form cotton seed meal. Either meal or crude oil prior to caustic refining from this expander solvent extraction process is high in gossypol and related toxic terpenoids (around 0.6–0.8% gossypol in the crude oil and 0.8% total gossypol and 0.1% free gossypol in the meal) and may be used in this invention. Besides PBSY oil, soap stock is a minor by-product of crude oil or miscella refining processes. Soap stock derived from crude oil refining is further acidulated to form free fatty acids, commonly called acid oil. Soap stock from miscella refining still contains residual solvent and is added back to the MARC in a desolventizer-toaster to produce the final cotton seed meal. The soap stock, which is a waste product in the production of the PBSY oil, is high in gossypol and related terpenes (typically about >4% gossypol) and may be used alone or added to meal for use in this invention. The desolventized MARC or final meal may also be used in this invention. The PBSY oil does not typically have enough gossypol and related terpenoid toxins for use in this invention. The PBSY oil from which gossypol and related toxins have been removed may be used for consumption by mammals.

Because the cotton phyllophage toxins must be ingested for use against social insect pests as described herein, the compounds are preferably formulated into a bait upon which the target insect will feed. As used herein, a bait refers to any substance which will induce the target insect to ingest a formulation of the active agent(s). Thus, suitable baits for use herein will include the gossypol and/or other cotton phyllophage toxins in combination with a feeding stimulant (phagostimulant) and/or food material in an amount effective to stimulate feeding thereon by the target insect, and an optional carrier. The skilled practitioner will recognize that some feeding stimulants and food materials may also function as a carrier.

The amount of gossypol and other cotton phyllophage toxins incorporated into the bait should provide a concentration therein effective to increase the susceptibility of the insects to other insecticidal agents (i.e., non-cotton phyllophage toxins). However, the concentration of the phyllophage toxins should be sufficiently low that, in the absence of the other insecticidal agents, the bait is not biocidal to the target insects. The mode of action of the other insecticidal agents used herein may vary, and include death inducement, growth regulation or inhibition, sterilization, as well as interference with metamorphosis and other morphogenic functions. Accordingly, as used herein, an effective concentration of cotton phyllophage toxin (gossypol or other) is defined as those quantities which will result in a significant increase in one or more of these responses by the target insects to the other insecticidal agents, relative to a negative control (i.e., without cotton phyllophage toxin), but which quantities are not biocidal to the target insect when the cotton phyllophage toxins are used alone (in the absence of such other insecticidal agents). In a preferred embodiment, the cotton phyllophage toxins are provided at a concentration effective to synergistically increase these responses by the target insects to the other insecticidal agents. The actual effective amount will vary with the species of insect pest, the application technique, and the insecticidal agent and its desired effect, and may be readily determined by the practitioner skilled in the art by routine experimentation. In a preferred embodiment, without being limited thereto, the lower limit of the total concentration of pure gossypol and other cotton phyllophage toxins in the bait is greater than or equal to about 5 ppm, more preferably about 50 ppm, and most preferably about 100 ppm, while the upper limit of the concentration thereof is less than 500 ppm, preferably less than or equal 450 ppm. Thus, in a particularly preferred embodiment, the concentration of pure gossypol and other cotton phyllophage toxins in the bait is between about 100 ppm and about 450 ppm.

The amount of the various cotton products used to provide the effective amount of the cotton phyllophage toxins described above will vary with the particular product selected. For instance, without being limited thereto, the amount of cotton seed to be incorporated will typically be between about 20 g/kg and about 50 g/kg. For other cotton products, representative examples of suitable amounts include but are not limited to the i following: cotton seed extract to be incorporated will typically be between about 0.05 g/kg and about 0.500 g/kg; crude cotton seed oil to be incorporated will typically be between about 0.500 g/kg and about 2.50 g/kg (which is less than an amount which can be detected by termites); cotton seed oil extract to be incorporated will typically be between about 0.050 g/kg and about 0.500 g/kg; cotton seed meal or flour to be incorporated will typically be between about 20 g/kg and about 50 g/kg; miscella to be incorporated will typically be between about 20 g/kg and about 50 g/kg; and soap stock to be incorporated will typically be between about 0.100 g/kg and about 1.250 g/kg.

Formulations of the baits may vary with the target insects, and a number of baits for social insect pests have been previously described which are suitable for use herein. Without being limited thereto, examples of bait formulations which are suitable for use against social insect pests are described hereinbelow. The practitioner skilled in the art will recognize that variations in the traditional components of baits are known and may be used with the cotton phyllophage toxins as described herein.

Termite baits will typically include a cellulose-containing material, which functions as both a food on which the termites will feed, and as a solid matrix which may be placed at least partially below the soil surface. Suitable cellulose-containing materials include, but are not limited to paper, paper products (e.g., virgin paper, recycled paper, or a combination of both), cotton linter, cardboard, paperboard, wood, sawdust, wood particles or wood flour, processed or purified cellulose, cellulose derivatives such as cellulose ethers, and including, for example, methylcellulose, hydroxypropylmethylcellulose, and hydroxybutylmethylcellulose, or other agricultural fibers.

Other optional, yet preferred additional components for a termite bait include water, a humectant, lipids, and termite-preferred nutrients. Subterranean termites are normally attracted to and reliant upon the presence of moisture. Therefore, addition of sufficient water to moisten the bait matrix and further increase the attractiveness of the composition to the termites is preferred. Particularly preferred baits will include greater than or equal to about 50%, and less than or equal to about 90% water, by weight of the bait. In this event, the water may be provided with a humectant such as agar, methylcellulose, or polyacrylamide to maintain the moisture content in the bait.

Preferred lipid sources include fats or phospholipids which are a source of choline chloride, and fatty acids such as linolenic, palmitic, palmitoleic and oleic acids, which are present in lecithin. Vegetable oils such as corn oil, soybean oil, cotton oil, and other oils known to the art may also be used, as these contain desirable fatty acids such as linolenic acid. Choline chloride may be added separately to the bait if it is not present in the oils. The concentration of lipid in the bait should be sufficient to be detectable by termites and less than that causing termite refusal of the food. In the case of lecithin, this amount ranges from about .1 g/kg to about 12.5 g/kg of bait, preferably from about 1 g/kg to about 2 g/kg of bait, and is most preferably about 1.25 g/kg of bait.

Termite baits also may comprise vitamins and amino acids characteristic of naturally-occurring termite food or which are attractive to termites, including vitamins such as riboflavin, D-biotin, choline chloride, vitamin B-12, folic acid, myo-inositol, nicotinamide, calcium pantothenate, pyridoxal hydrochloride, thiamine and ascorbic acid; and amino acids such in as L-glutamic acid, L-histidine, L-glutamine, L-alanine, L-lysine, L-isoleucine, L-proline,- and L-tyrosine. Vitamin and amino acid-containing materials include yeast and yeast hydrolysate, as well as synthetic solutions that contain these chemicals. Yeast hydrolysate is preferred because of its ability to also act as a food conditioning agent. The vitamins and amino acids may be present in the bait at aggregate ratios sufficient to be detectable by termites up to amounts which cause these insects to stop feeding. In the case of yeast hydrolysate, preferred amounts are between about 0.1 g/kg and about 3 g/kg of bait, more preferably from about 1.0 g/kg to about 2.0 g/kg of bait, and most preferably about 1.5 g/kg of bait.

As an alternative or in addition to amino acids, termite baits may also preferably include low concentrations of other nitrogen containing compounds. At these low levels, the nitrogen containing compounds are effective as both feeding stimulants and reduce or mask the repellency of other bait components and termiticides. Preferred nitrogen containing compounds include urea and uric acid. Other nitrogen containing compounds suitable for use herein include but are not limited to derivatives of urea, also referred to as ureido compounds, such as benzylurea and dibenzylurea (carbanilide); derivatives and isomers of uric acid, such as tauto-uric acid; amino benzoic acid; aminobenzoyl glutamic acid; amino butyric acid; aminonicotinic acid; aminophenol; aminosalicylic acid; aminonaphthols and aminonaphthoic acid; aminopurine (adenine); aminopyridine; benzylamines such as 6-benzylaminopurine 9-(B-D-glucoside) and 6-benzylaminopurine riboside; synthetic sweeteners such as aspartame; glucosamine; and ammonium salts such as ammonium fluoride and the ammonium salt of molibdic acid. The actual effective amount of nitrogen containing compounds added may vary with the particular bait formulation, particularly with the presence of amino acids, polypeptides, and proteins, which may also be effective as termite aggregants and masking agents. In the absence of other amino acids, polypeptides, or proteins, the concentration of the nitrogen containing compounds should be between about 10 to 1,000 ppm, preferably between about 100 to 500 ppm, and most preferably about 450 ppm. However, for baits in which amino acids, polypeptides, or proteins are present, the concentration of the above-mentioned nitrogen containing compounds should be reduced accordingly. In any event, the total concentration of the nitrogen containing compounds, including any amino acids, polypeptides, or proteins, should not exceed about 1,000 ppm.

Inert carriers may be included as necessary for the components of the bait, and may be readily selected by the practitioner skilled in the art. Without being limited thereto, preferred carriers for gossypol, particularly when used in pure form, include acetic acid or acetone. For instance, commercial grade gossypol is often available complexed with acetic acid. When using either this complexed form or cotton seed soap stock, the complex or soap stock are first dissolved in acetone prior to mixing with the bait. Conversely, phyllophage toxins in the form of cotton seed oil, flour or meal, are generally mixed directly with the cellulose and bait.

Other optional components which may be included in a termite bait include the above-mentioned other insecticidal agents, colorants, insect attractants such as termite pheromones or termite extracts containing pheromones, food odor attractants, or aggregation attractants.

Particularly preferred termite baits for use herein are described by Rojas et al. (U.S. patent application Ser. Nos. 09/748,036, filed Dec. 22, 2000, and 09/625,940, filed Jul. 26, 2000, the contents of each of which are incorporated by reference herein).

Bait formulations effective for control of fire ants have been previously described and are suitable for use herein, and include, but are not limited to, those described by Greenbaum and Weil (U.S. Pat. No. 3,220,921), (U.S. Pat. No. 5,897,859), (U.S. Pat. No. 6,149,913), (U.S. Pat. No. 6,216,384), the contents of each of which are incorporated by reference herein.

Many materials have been disclosed as being effective as feeding stimulants and attractive feeding materials for use in fire ant baits. These include edible oils and fats, alkanes, vegetable seed meals, meal by-products such as blood, fish meal, syrups, honey, sucrose and other sugars, peanut butter, cereals, amino acids, proteins, and isolated compounds such as trans, trans-2,4-heptadienal and/or trans, cis-2,4-heptadienal. While it is envisioned that any of these materials and/or compounds may be used herein, in the preferred embodiment, vegetable oils are used as feeding stimulants for fire ant baits, which oils may also functions as carriers for insecticidal agents. Particularly preferred vegetable oils include corn oil, soybean oil, palm oil, coconut oil, canola oil, sesame oil, and peanut oil.

The bait may be a liquid, gel, or solid, although use of solid baits are generally preferred. Liquid feeding stimulants, the cotton phyllophage toxins, and other components may be incorporated into a solid carrier. The carrier selected is not critical, and examples of suitable carriers include, organic fillers such as corncob grits, bran, crushed puffed grain, pregel defatted corn grits, extruded corn, powdered carbohydrates such as corn starch, dextrans, and cellulose, as well as diatomaceous earth, alumina, silica, clays, other suitable inorganic oxides, polymers, and the like.

As with termite baits, a number of optional additives or adjuvants may also be included, such as wetting agents, surfactants, stabilizers, dispersants, dye-stuffs, thixotropic agents, pheromones or ant extracts containing pheromones, and sticking agents, adhesives or glues.

Baits effective for control of cockroaches have also is been previously described and are suitable for use herein, and include, but are not limited to, those described by Wolfe et al. (U.S. Pat. No. 5,676,961), Kohama et al. (U.S. Pat. No. 4,985,413), and Sembo (U.S. Pat. No. 6,225,344), the contents of each of which are incorporated by reference herein.

Cockroach baits may be formulated with a single food material and/or feeding stimulant, although many conventional cockroach baits typically include a plurality of components therefor. Examples of food materials and feeding stimulants which have been previously described and which may be used in cockroach baits herein include but are not limited to proteins (animal or plant) such as meats, meat extracts, animal digests (including fish and insect digests), grains, flour, and meals such as oatmeal, starch, cellulose, carbohydrates such as molasses, corn syrup, maple syrup, honey, monosaccharides, and oligosaccharides, milk, and lipids such as vegetable oils.

The formulation of the bait, including the use of optional carriers and other components, may be similar to those described for ants hereinabove.

The phyllophage toxins of this invention may be used in conjunction with a variety of known insecticidal agents, including synthetic or naturally occurring chemical agents and viruses, bacteria, fungi, nematodes, and protozoa effective for control of the target social insect. As used herein, the term "insecticidal agent" refers to a material or mixture of materials which induce mortality, disrupt or impede growth, interfere with metamorphosis or other morphogenic functions, effect to sterilization, or interfere with reproduction of the targeted to insect. Without being limited thereto, preferred insecticidal agents for use herein are slow-acting (i.e., acting over a course of hours, days, weeks, or preferably months), to reduce "avoidance" effects before individuals have distributed food to as other members of the colony.

The cotton phyllophage toxins and the other insecticidal agents may be formulated into the same bait or in separate compositions. While the other insecticidal agents may also be formulated as a bait, the skilled practitioner will recognize that such bait formulations may not be necessary for contact-type insecticidal agents which are formulated apart from the cotton phyllophage toxin containing bait. Suitable formulations for the insecticidal agents are well-known in the art and may be readily selected by the practitioner skilled in the art. When formulated separately, the compositions are applied in the vicinity or close proximity of one another and the target insects, such that both are subject to consumption and/or contact by the same insect population. For the purpose of this invention, the components are said to be placed in "close proximity" when they are close enough together to be fed upon and/or contacted by the same insects within a normal feeding period of about one month, e.g., when they within a 50 m radius of each other.

The particular insecticidal agent used may vary with the target insect, although a number of agents possess broad-spectrum activity against more than one pest. A plurality of insecticidal agents have been described for use against the social insects, as well as their optimal application techniques and rates. Without being limited thereto, representative examples of suitable insecticidal agents suitable for use against social insect pests are described hereinbelow.

For control of termites, suitable insecticidal agents or termiticides include but are not limited biological controls such as termite growth regulators, and materials that are toxic to termites (i.e., toxicants) such as chemical insecticides, pathogenic nematodes, fungi, protozoans, or bacteria. A variety of slow-acting termiticides are known in the art and may be used herein, including, for example, silafluofen, borates (boric acid, disodium octaborate tetrahydrate), sulfluramid and other fluoroalkyl sulfonamides, avermectin, hydramethylnon, hexaflumuron, chlorfluazuron, lufenuron, and other chitin synthesis inhibitors and-other acyl ureas, diflubenzuron (Dimilin), azadirachtin, dechlorane (Mirex), diiodomethyl-para-tolyl sulfone (A-9248), fluorosulfonates, imidacloprid, azadirachtin, cyromazine, juvenile hormones and juvenile hormone mimics or analogs such as fenoxycarb, methoprene, hydroprene, triprene, furnesinic acid ethyl and alkoxy derivatives, and pyriproxyfen (Nylar), antimicrobials such as streptomycin sulfate, rifampicin, albendazole, neomycin sulfate, sorbic acid, antibiotics, antimycotics, insecticides such as hydramethylnon, disodium octaborate tetrahydrate, imidacloprid, and fipronil, and the plant *Rheuneo jupanic* Thunb. Roth. In addition, otherwise faster-acting insecticides may act more slowly when used by microencapsulation. Biological control agents that may be used as termiticides include fungi such as *Metarhizium anisopliae, Aspergillus flavus*, and *Beauveria bassiania*, nematodes such as *Neoplectana carpocapsae*, insect viruses, pathogenic bacteria such as *Bacillus thuringiensis* and *Serratia marcescens*, and toxins derived from biological control agents such as *B. thuringiensis* toxin. Other microbes to which the target insects may be rendered susceptible include Paecilomyces spp, *Aspergillus fumigatue, Aspergillus nomius*, Aspergillus spp., and *Aspergillus niger*

Other insecticidal agents suitable for use herein against termites include monoterpenes derived from cotton effective to inhibit mixed function oxidases (MFOs) in the pest (see Hedin et al., 1988, "Elucidating Mechanisms of Tobacco Budworm Resistance to Allelochemicals by Dietary Tests with Insecticide Synergists", *Pest. Biochem. Physiol.*, 32:55–61). Such monoterpenes contain single naphthalenic fused ring structures and are preferably selected from the group consisting of the group consisting of α-pinene, β-pinene, myrcene, β-ocimene, α-copaene, α-humulene, β-caryophylene, β-carophyllene oxide, γ-bisabolene, β-bisabolol, limonene, and piperonyl butoxide and mixtures of the foregoing.

For control of ant pests, and particularly fire ants, suitable insecticidal agents include, but are not limited to organophosphates, carbamates, arsenicals, pyrethroids, insect growth regulators, boric acid, silica gel and borate, such as described by Hagarty (U.S. Pat. No. 5,104,658, the contents of which are incorporated by reference herein), fluorocarbons, and sulfluramids, such as described by Meer et al. (U.S. Pat. Nos. 4,921,696, 5,177,107, and 5,364,618, the contents of each of which are herein incorporated by reference).

Insecticidal agents suitable for the control of cockroaches include but are not limited to benzoylphenylurea insecticides, pentadien-3-one substituted amidino hydrazones, organophosphates, carbamates, pyrethroids, chlorinated hydrocarbons, fluoroaliphatic sulfonamides, borates, insect growth regulators, and avermectins, such as described by Kohama (ibid), Spragia (U.S. Pat. No. 6,245, 816), and Wolfe (ibid), the contents of each of which are incorporated by reference herein. Preferred organophosphates include caltinphos, chlorpyriphos, chlorpyriphosmethyl, cyanofenphos, cyanophos, diazinon, dichlorvos, fenitrothion, fenthion, malathion, naled, pirimiphosmethyl, prothiophos, pyridaphenthion, salithion, tetrachlorvinphos, trichlorfcn, bromophos, and propetamphos, preferred carbamates include BPMC, carbaryl, CPMC, ethiofencarb, MPMC, MTMC, promecarb, swep, propoxur, and preferred pyrethroids include cypermethrin, cyphenothrin, deltamethrin, fenpropathrin, fenvalerate, kadethrin, permethrin, phenothrin, proparthrin, resmethrin, ethofenprox, cyfluthrin, alpha-methrin, tralomethrin, and fulcythrinate.

The amounts of the insecticidal agents used herein will vary with the particular agent selected, the target insect pest, and the environmental conditions, and may be readily determined by the practitioner skilled in the art. In any event, the, amounts will be significantly lower than the rates of application normally described for the selected agents. In the absence of the cotton phyllophage toxins, the amounts of the other insecticidal agents used herein would provide substantially reduced efficacy relative to that obtained using the normally described amounts. Moreover, in the preferred embodiment, the insecticidal agents are provided at concentrations or amounts which would normally be ineffective for control of the insect pests (i.e., in the absence of the cotton phyllophage toxins). As used herein, a "normally ineffective" amount of the other insecticidal agent is defined those quantities which will not result in a significant increase in one or more of the desired responses (i.e., death inducement, growth regulation or inhibition, sterilization, or interference with metamorphosis and other morphogenic functions) by the target insects to the agent, relative to a negative control (i.e., without the agent). In this preferred embodiment, when normally ineffective amounts of known insecticidal agents are combined with normally non-biocidal amounts of gossypol and other cotton phyllophage toxins, the result is an insecticidally effective composition, i.e.,a composition capable of controlling a significant number of target insects which ingest it, even though the total amount of toxic substance present in the composition is less than the normally effective amount of either the known insecticidal agent or the phyllophage toxin.

The reduction in the amounts of the other insecticidal agents which are necessary for efficacy in accordance with this invention are significantly reduced relative to the prior art. For example, some chitin inhibitors are now used in amounts of around 5000 ppm for killing termites. In the compositions of this invention using gossypol and/or other cotton phyllophage toxins, the amount of chitin inhibitors required to control termite nests can be reduced by up to 90%, thus reducing or eliminating the environmental impact of their application.

Similarly, as is known to the art, lethal amounts of such known insecticidal agents (as recommended by manufacturers) are: diflubenzuron, about 0.250%; hexaflumuron, about 0.5%; chlorfuazuron, about 0.5%; imidacloprid, about 0.05% to 0.1% for subterranean termites, about 2.15% for roaches; disodium octaborate tetrahydrate, about 0.5% for subterranean termites; hydramethylnon, about 0.030% for subterranean termites and about 1.0% for ants; and fipronil, about 0.05% for roaches. "Normally ineffective amounts" of such known insecticidal agents which are used herein are thus substantially less than these normally lethal amounts. When using the above described monoterpenes, the amounts used herein should be between about 0.005 g/kg and about 0.300 g/kg of bait, preferably between about 0.050 g/kg and about 0.100 g/kg.

This invention also provides methods of controlling a colony of social insects, which includes providing to the locus or vicinity of a target insect colony a single or separate compositions of: (1) the other insecticidal agent at a substantially reduced amount than normally required for efficacy; and (2) a bait having an amount of a phyllophage toxin from glanded cotton sufficient to increase or impart insecticidal effectiveness to said composition. By "insecticidal effectiveness" is meant the ability to control the insect population of the colony. By "controlling the population of a colony" is meant killing or impairing a sufficient number of individual insects by one or more of the insecticidal mechanisms described above.

The following example is intended only to further illustrate the invention and is not intended to limit the scope of the invention, which is defined by the claims.

EXAMPLES

Gossypol acetic acid complex, which is a commercially available pure chemical, is dissolved in 1 ml acetone (#9006-03; J. T. Baker, Phillipsburg, NJ) using a sterile container. In the pure form as gossypol acetic acid complex and at concentrations of 5 ppm, gossypol is effective when mixed with a chitin synthesis inhibitor of the benzophenyl urea family or microbes such as fungi, bacteria, or viruses, taking a mean time to kill the lab test of four months. At concentrations greater than 500 ppm, without the addition of any other chemical, gossypol acetic acid complex as an insecticide can kill the lab test colony after a mean duration of one month.

Gossypol-acetic acid complex obtained from USDA-ARS-SRCC, New Orleans, La., crude cotton seed oil [8ETX (5)], from a commercial oil mill, and a commercial cotton meal [6MTN 925 CSM] were separately incorporated into a bait matrix as described in U.S. patent application Ser. No. 09/294,499 filed Apr. 20, 1999, at concentrations of 50, 25, and 12.5 ppm respectively. Preliminary results in testing a range of gossypol doses from 5 to 500 ppm had shown that 100, 25, and 12.5 ppm, respectively, were sufficient to weaken the termites and allow other chemicals or microorganisms to induce mortality in about two months without signs of repellency by the termites which was seen at higher gossypol doses but not at low gossypol doses. A total of 40 mg of the gossypol acetic acid complex, 250 mg of the crude cotton seed oil, and 900 mg of the cotton seed meal were individually weighed using a Mettler balance (model PB303; Fisher Scientific, Pittsburgh, Pa.). The gossypol-acetic acid complex was placed into a 50 ml sterile screw cap conical tube (#62.547.004; Sarstedt, Newton, N.C.) and dissolved with 1 ml acetone (#9006-03; J. T. Baker, Phillipsburg, N.J.).

Gossypol-Chitin Inhibitors

Under a laminar flow hood, the gossypol acetone solution was mixed with 40 ml of sterile nutritional supplement containing 150 ppm of chitin inhibitors (prepared as reported by Rojas, M. G. and Morales-Ramos, J. A., Apr. 2001, "Bait matrix for delivery of chitin synthesis inhibitors to the Formosan subterranean termite [Isoptera: Rhinotermitidae]," *J. Econ. Entomol.* 94(2):506–510). The tube was tightly closed with a screw cap and manually shaken for 30 seconds. The mixture was added to 100 g of sterile cellulose as reported by Rojas and Morales-Ramos (2001) supra. The cotton seed oil was mixed with 300 ml of supplement and mixed with the sterile cellulose. The cotton seed meal was mixed and homogenized with the sterile cellulose, and then the 300 ml nutritional supplement was added. Each mixture was manually homogenized using a stainless steel spatula.

Gossypol-Fungal Spores

The mixtures were prepared as reported above for gossypol-chitin inhibitors, but without the addition of the chitin inhibitors. The fungal spores (400 mg) (Bio-Blast, EcoScience, Orlando, Fla.) were homogenized with the sterile cellulose, then the 300 ml of supplement gossypol-containing solution was added.

To encase the bait matrix, tubes made of fibrous casing material (#124B; L. E. M. Products, Inc., Miamitown, Ohio) were cut into 150 mm long portions as reported by Rojas and Morales-Ramos (2001) supra. Fifty grams of bait matrix containing a mixture of a single gossypol source and a single chitin synthesis inhibitor, or single gossypol source and fungal spores, were compacted into one end of the inlet tube, at which point the open end of the inlet tube was closed with a rubber band. The bait casing was placed inside of the foraging box adjacent to a 10 g piece of pine wood, taking care that they were partially covered with the sand. Control bait matrix was prepared minus any gossypol, but with the chitin synthesis inhibitors or fungal spores, and presented in the same way as the treatment matrices. Test termites were taken from three different colonies, with two boxes per locality with a total of six boxes of 2500 termites per treatment. (Rojas and Morales-Ramos [2001] supra.)

All the experimental boxes were maintained under dark at 29±2° C., and 75±2% relative humidity. Observations were done every 72 hours until all the termites died. The time to reach 100% mortality was measured and recorded. Mean comparisons among treatments and control were conducted.

It was observed that the experimental colonies containing gossypol with the chitin inhibitor were dead in about two months while the control boxes were still alive. The same effect was seen with the mixture of gossypol in the form of crude cotton seed oil and fungi. Treatment boxes were dead and control alive. Small colonies of the fungi were observed to be coming out of termite bodies collected from the treated boxes, while this was not observed in the control boxes.

Then the source of gossypol is in the form of acetic acid complex, at concentrations of 500 ppm, this terpenoid acts very strongly in the termites, producing a mortality of a 1000-worker colony in about 2.5 weeks, even though it is not mixed with any other chemicals, fungi, or bacteria which are normally found in termite tunnels, pieces of wood, cardboard, bait casing, and the like.

It is preferred to add up to about 1.5 ml of crude cotton seed oil to each kg of bait matrix, as use of more than about 2.5 ml crude cotton seed oil could drastically reduce the acceptance of the bait matrix by the termites. The optimal amount for cotton meal is about 40 g per kg and no more than about 50 g per kg.

It is understood that the foregoing detailed description is given merely by way of illustration and that modifications and deviations may be made therein without departing from the spirit and scope of the invention.

What is claimed is:

1. An insect bait composition for the control of insect pests comprising gossypol, an amount of a feeding stimulant or food material effective to stimulate feeding thereon by a target insect, and an insecticidal agent, wherein the concentration of said gossypol in said bait is not biocidal to said target insect in the absence of said insecticidal agent, but is sufficient to significantly increase the insecticidal efficacy of said insecticidal agent to said target insect so that the combination of said gossypol and said insecticidal agent is effective for control of said target insect and further wherein said additional insecticidal agent is selected from the group consisting of *Metarhizium anisopliae, Aspergillus flavus, Beauveria bassiania*, Paecilomyces spp, *Aspergillus fumigatus, Aspergillus nomius*, and *Aspergillus niger*.

2. The insect bait composition of claim 1 wherein said insecticidal agent is provided at a concentration in said bait which is ineffective for control of said target insect in the absence of said gossypol.

3. The insect bait composition of claim 1 wherein the concentration of said gossypol in said bait is greater than or equal to about 5 ppm, and less than 500 ppm.

4. The insect bait composition of claim 3 wherein the concentration of said gossypol in said bait is greater than or equal to about 5 ppm, and less than or equal to about 450 ppm.

5. The insect bait composition of claim 4 wherein the concentration of said gossypol in said bait is greater than or equal to about 50 ppm, and less than or equal to about 450 ppm.

6. The insect bait composition of claim 1 wherein said gossypol is contained in an extract of cotton seed or cotton seed oil.

7. The insect bait of claim 1 wherein said target insect is a social insect, said feeding stimulant and feeding material are effective for stimulating feeding of said social insect upon said bait, and said insecticidal agent is effective against said social insect.

8. The insect bait composition of claim 7 wherein said social insect is selected from the group consisting of termites, fire ants, and cockroaches.

9. A termite bait composition comprising a glanded cotton phyllophage toxin, water, an insecticidal agent, and a cellulose-containing material effective as a food material upon which the termite will feed, wherein the concentration of said phyllophage toxin in said bait is not biocidal to said termite in the absence of said insecticidal agent, but is sufficient to significantly increase the insecticidal efficacy of said insecticidal agent when said termite is exposed thereto, and further wherein said water is present in said bait in an amount greater than or equal to about 50%, and less than or equal to about 90% by weight of said bait.

10. The termite bait composition of claim 9 wherein the concentration of said phyllophage toxin in said bait is greater than or equal to about 5 ppm, and less than or equal to about 500 ppm.

11. The termite bait composition of claim 10 wherein the concentration of said phyllophage toxin in said bait is greater than or equal to about 5 ppm, and less than or equal to about 450 ppm.

12. The termite bait composition of claim 11 wherein the concentration of said phyllophage toxin in said bait is greater than or equal to about 50 ppm, and less than or equal to about 450 ppm.

13. The termite bait composition of claim 9 further comprising a humectant.

14. The termite bait composition of claim 13 wherein said humectant is selected from the group consisting of agar, polyacrylamide, and methylcellulose.

15. The termite bait composition of claim 9 wherein said insecticidal agent is selected from the group consisting of silafluofen, borates, sulfluramid, fluoroalkyl sulfonamides, avermectin, hydramethylnon, hexaflumuron, chlorfluazuron, lufenuron, diflubenzuron, azadirachtin, dechlorane, diiodomethyl-para-tolyl sulfone, fluorosulfonates, imidacloprid, cyromazine, juvenile hormones, fenoxycarb, methoprene, hydroprene, triprene, furnesinic acid ethyl and alkoxy derivatives, pyriproxyfen, streptomycin sulfate, rifampicin, albendazole, neomycin sulfate, sorbic acid, antibiotics, antimycotics, disodium octaborate tetrahydrate, fipronil, the plant Rheuneo jupanic Thunb. Roth, *Metarhizium anisopliae, Aspergillus flavus, Beauveria bassiania, Neoplectana carpocapsae, insect viruses Bacillus thuringensis, Serratia marcescens, Bacillus thuringensis toxin*, Paecilomyces spp, *Aspergillus fumigatus, Aspergillus nomius*, and *Aspergillus niger*.

16. The termite bait composition of claim 9 wherein said bait is a solid.

17. A method of controlling social insects, said method comprising providing an insect bait composition to the locus of a colony of said insects, wherein said insect bait composition comprises a glanded cotton phyllophage toxin, water, an amount of a feeding stimulant or food material effective to stimulate feeding thereon by said social insects, and an insecticidal agent, wherein the concentration of said phyllophage toxin in said bait is not biocidal to said social insects in the absence of said insecticidal agent, but is sufficient to significantly increase the insecticidal efficacy of said insecticidal agent to said social insects so that the combination of said phyllophage toxin and said insecticidal agent is effective for control of said social insects, and further wherein said water is present in said bait in an amount greater than or equal to about 50%, and less than or equal to about 90% by weight of said bait.

18. A method of controlling subterranean termites, said method comprising:
  a) providing a termite bait composition to the locus of a termite colony, wherein said termite bait composition comprises a glanded cotton phyllophage toxin and a cellulose-containing material effective as a food material upon which the termite will feed, and
  b) providing an additional insecticidal agent to the locus of said termite colony, wherein the concentration of said phyllophage toxin in said bait is not biocidal to termites in the absence of said additional insecticidal agent, but is sufficient to significantly increase the insecticidal efficacy of said additional insecticidal agent when termites are exposed thereto.

19. The method of claim 18 wherein said insecticidal agent is provided at a concentration in said bait which is ineffective for control of said termites in the absence of said phyllophage toxin.

20. The method of claim 18 wherein the concentration of said phyllophage toxin in said bait composition is greater than or equal to about 5 ppm, and less than or equal to about 500 ppm.

21. The method of claim 18 wherein the concentration of said phyllophage toxin in said bait composition is greater than or equal to about 5 ppm, and less than or equal to about 450 ppm.

22. The method of claim 18 wherein the concentration of said phyllophage toxin in said bait composition is greater than or equal to about 50 ppm, and less than or equal to about 450 ppm.

23. The method of claim 18 wherein said bait composition further comprises water.

24. The method of claim 23 wherein said water is present in said bait composition in an amount greater than or equal to about 50%, and less than or equal to about 90% by weight of said bait.

25. The method of claim 18 wherein said insecticidal agent is selected from the group consisting of silafluofen, borates, sulfluramid, fluoroalkyl sulfonamides, avermectin, hydramethylnon, hexaflumuron, chlorfluazuron, lufenuron, diflubenzuron, azadirachtin, dechlorane, diiodomethyl-para-tolyl sulfone, fluorosulfonates, imidacloprid, cyromazine, juvenile hormones, fenoxycarb, methoprene, hydroprene, triprene, furnesinic acid ethyl and alkoxy derivatives, pyriproxyfen, streptomycin sulfate, rifampicin, albendazole, neomycin sulfate, sorbic acid, antibiotics, antimycotics, disodium octaborate tetrahydrate, fipronil, the plant Rheu-neo jupanic Thunb. Roth, *Metarhizium anisopliae, Aspergillus flavus, Beauveria bassiania, Neoplectana carpocapsae*, insect viruses, *Bacillus thuringensis, Serratia marcescens, Bacillus thuringensis toxin*, Paecilomyces spp, *Aspergillus fumigatus, Aspergillus nomius*, and *Aspergillus niger*.

26. The method of claim 18 wherein said insecticidal agent comprises a monoterpene derived from cotton effective to inhibit mixed function oxidases (MFOs) in termites.

27. The method of claim 26 wherein said monoterpene agent is selected from the group consisting of α-pinene, β-pinene, myrcene, β-ocimene, α-copaene, α-humulene, β-caryophyllene, β-caryophyllene oxide, γ-bisabolene, β-bisabolol, limonene, piperonyl butoxide, and mixtures thereof.

28. A termite bait composition comprising a glanded cotton phyllophage toxin, water, a cellulose-containing material effective as a food material upon which the termite will feed, and an additional insecticidal agent, wherein the concentration of said phyllophage toxin in said bait is not biocidal to said termite in the absence of said additional insecticidal agent, but is sufficient to significantly increase the insecticidal efficacy of said additional insecticidal agent when said termite is exposed thereto, and further wherein said additional insecticidal agent comprises a monoterpene derived from cotton effective to inhibit mixed function oxidases (MFOs) in termites, and further wherein said water is present in said bait in an amount greater than or equal to about 50%, and less than or equal to about 90% by weight of said bait.

29. The termite bait composition of claim 23 wherein said monoterpene agent is selected from the group consisting of α-pinene, β-pinene, myrcene, β-ocimene, α-copaene, α-humulene, β-caryophyllene, β-caryophyllene oxide, γ-bisabolene, β-bisabolol, limonene, piperonyl butoxide, and mixtures thereof.

* * * * *